US011850099B2

(12) United States Patent
Watanabe et al.

(10) Patent No.: US 11,850,099 B2
(45) Date of Patent: Dec. 26, 2023

(54) ULTRASONIC DIAGNOSTIC APPARATUS

(71) Applicant: Canon Medical Systems Corporation, Otawara (JP)

(72) Inventors: Masaki Watanabe, Utsunomiya (JP); Yasunori Honjo, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

(21) Appl. No.: 16/798,752

(22) Filed: Feb. 24, 2020

(65) Prior Publication Data
US 2020/0268355 A1      Aug. 27, 2020

(30) Foreign Application Priority Data

Feb. 26, 2019   (JP) ................................. 2019-032941
Feb. 20, 2020   (JP) ................................. 2020-027282

(51) Int. Cl.
*A61B 8/08*      (2006.01)
*A61B 8/00*      (2006.01)

(52) U.S. Cl.
CPC ............ *A61B 8/5215* (2013.01); *A61B 8/463* (2013.01); *A61B 8/469* (2013.01); *A61B 8/485* (2013.01); *A61B 8/5207* (2013.01)

(58) Field of Classification Search
CPC ....... A61B 8/5215; A61B 8/463; A61B 8/469; A61B 8/485; A61B 8/5207
See application file for complete search history.

(56) References Cited

U.S. PATENT DOCUMENTS

2013/0144162 A1*  6/2013  Anquez ................. A61B 8/085
                                                         600/438
2015/0216508 A1*  8/2015  Iwama ................ G01S 7/52042
                                                         600/438
(Continued)

FOREIGN PATENT DOCUMENTS

JP          2016-77534 A      5/2016
JP          2017-93913 A      6/2017
(Continued)

OTHER PUBLICATIONS

Office Action dated Jun. 6, 2023, issued in corresponding Japanese patent application No. 2020-027282.

*Primary Examiner* — Joseph M Santos Rodriguez
*Assistant Examiner* — Brooke Lyn Klein
(74) *Attorney, Agent, or Firm* — Oblon, McClelland, Maier & Neustadt, L.L.P.

(57) ABSTRACT

According to one embodiment, an ultrasonic diagnostic apparatus includes an ultrasonic probe and processing circuitry. The processing circuitry causes the ultrasonic probe to perform a first scan and second scan in a same scan sequence, wherein the first scan is for calculating a first index value based on a displacement of tissue by a shear wave that propagates through a living body, the second scan for calculating a second index value indicating an attenuation of a reflected wave signal of an ultrasonic wave applied into the living body. The processing circuitry generates a first image based on the first index value, and generates a second image based on the second index value. The processing circuitry causes a display to simultaneously display the first image and the second image.

12 Claims, 7 Drawing Sheets

(56) References Cited

U.S. PATENT DOCUMENTS

| | | | |
|---|---|---|---|
| 2016/0095582 A1* | 4/2016 | Iwama | A61B 8/4416 |
| | | | 600/438 |
| 2016/0331353 A1* | 11/2016 | Ralston | A61B 8/546 |
| 2017/0150948 A1* | 6/2017 | Kanayama | A61B 8/488 |
| 2018/0035980 A1* | 2/2018 | Sonoyama | A61B 8/08 |
| 2018/0132831 A1* | 5/2018 | Yang | G01S 7/52085 |
| 2019/0029649 A1* | 1/2019 | Tanigawa | G16H 50/30 |
| 2019/0183461 A1* | 6/2019 | Sonoyama | G01S 7/52042 |
| 2020/0256971 A1* | 8/2020 | Huang | G01N 29/11 |

FOREIGN PATENT DOCUMENTS

| | | |
|---|---|---|
| JP | 2017-104526 A | 6/2017 |
| JP | 2018-20107 A | 2/2018 |
| JP | 2018-86322 A | 6/2018 |
| JP | 2018-99180 A | 6/2018 |
| JP | 2019-24682 A | 2/2019 |

\* cited by examiner

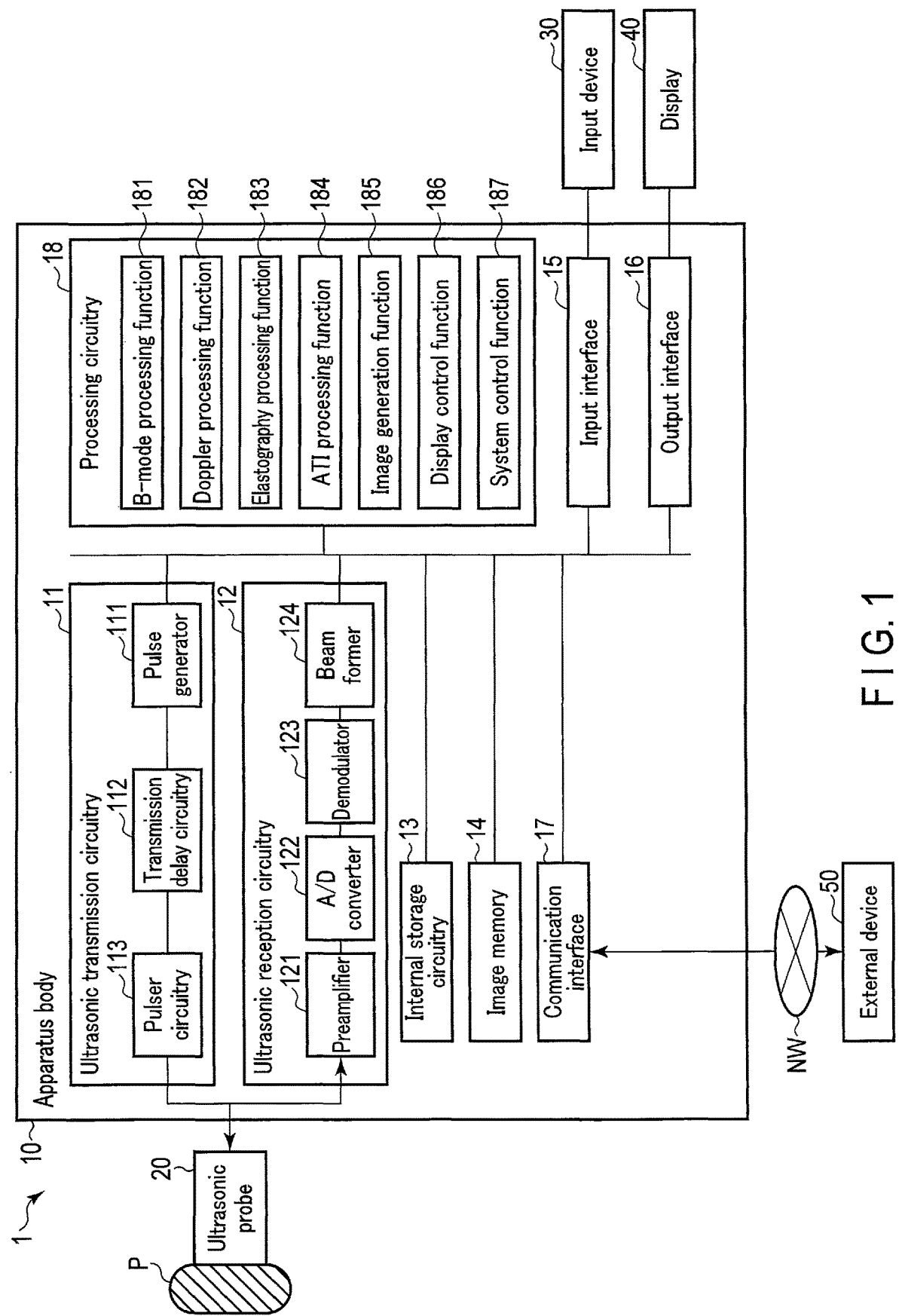
F I G. 1

| B mode | SWE | Cooling Time | ATI |

FIG. 2

| B mode | SWE | ATI | Cooling Time |

FIG. 3

| B mode | ATI | SWE | Cooling Time |

FIG. 4

| ATI | B mode | SWE | Cooling Time |

FIG. 5

ULTRASONIC DIAGNOSTIC APPARATUS

CROSS-REFERENCE TO RELATED APPLICATIONS

This application is based upon and claims the benefit of priority from Japanese Patent Applications No. 2019-32941, filed Feb. 26, 2019; and No. 2020-27282, filed Feb. 20, 2020; the entire contents of both of which are incorporated herein by reference.

FIELD

Embodiments disclosed herein relate generally to an ultrasonic diagnostic apparatus.

BACKGROUND

In recent years, the number of patients with cirrhosis resulting from viral hepatitis is decreasing due to developments in antivirus medicines. In contrast, the number of patients with fatty cirrhosis resulting from lifestyle-related diseases is increasing. Fatty cirrhosis causes inflammation, and develops into hepatic fibrosis; therefore, it is important to quantify the degree.

An ultrasonic diagnostic apparatus has a function of quantifying tissue properties of a subject as well as a function of visualizing the morphology of an organ in the subject based on a reflected wave signal of an ultrasonic wave applied to the subject. For example, an elastography function uses a shear wave that propagates through a living body, and acquires an index value indicating, for example, elasticity or viscosity of living tissue. The index value indicating, for example, elasticity or viscosity of living tissue is used for determination of the degree of hepatic fibrosis, inflammation, or the like. In addition, an index value indicating an attenuation of an ultrasonic wave in living tissue is acquired by, for example, analyzing how a reflected wave signal is reduced. The index value indicating an attenuation of an ultrasonic wave is regarded as useful for the determination of the degree of fatty liver.

To determine the tissue properties of a subject, it is helpful to display, in parallel, images based on various index values indicating physical properties of tissue. For example, In order to collectively determine the tissue properties of a liver from index values having the respective characteristics, it is appropriate to display either an image relating to elasticity or viscosity acquired through the elastography function or images relating to both in parallel with an image relating to an attenuation of an ultrasonic wave.

However, the index value indicating elasticity, viscosity, or the like and the index value indicating an attenuation of an ultrasonic wave are acquired by separate scan sequences. Therefore, the index value acquired through the elastography function is not associated with the index value indicating an attenuation of an ultrasonic wave, and observation requires separate ascertainment of both information items, thus requiring time.

BRIEF DESCRIPTION OF THE DRAWINGS

FIG. 1 is a block diagram showing a functional configuration of an ultrasonic diagnostic apparatus according to a first embodiment.

FIG. 2 is a diagram showing an example of a scan sequence of an SWE+ATI mode according to the first embodiment.

FIG. 3 is a diagram showing another example of the scan sequence of the SWE+ATI mode according to the first embodiment.

FIG. 4 is a diagram showing a further example of the scan sequence of the SWE+ATI mode according to the first embodiment.

FIG. 5 is a diagram showing another additional example of the scan sequence of the SWE+ATI mode according to the first embodiment.

DETAILED DESCRIPTION

Figure 6:
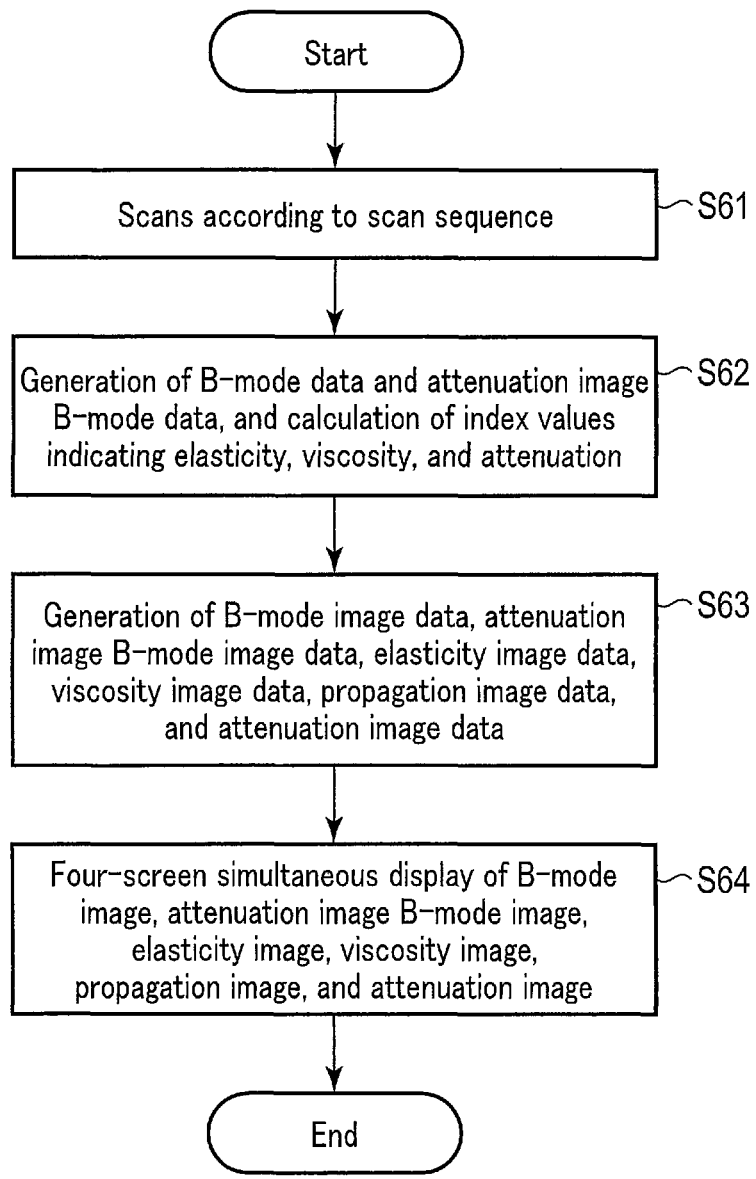
FIG. 6 is a flowchart showing an operation performed when the ultrasonic diagnostic apparatus shown in FIG. 1 causes a display to display a plurality of images based on various types of ultrasonic image data.

In general, according to one embodiment, an ultrasonic diagnostic apparatus includes an ultrasonic probe and processing circuitry. The processing circuitry causes the ultrasonic probe to perform a first scan and second scan in a same scan sequence, wherein the first scan is for calculating a first index value based on a displacement of tissue by a shear wave that propagates through a living body, the second scan for calculating a second index value indicating an attenuation of a reflected wave signal of an ultrasonic wave applied into the living body. The processing circuitry generates a first image based on the first index value, and generates a second image based on the second index value. The processing circuitry causes a display to simultaneously display the first image and the second image.

Hereinafter, embodiments will be described with reference to the accompanying drawings.

First Embodiment

FIG. 1 is a block diagram showing an example of a functional configuration of an ultrasonic diagnostic apparatus 1 according to a first embodiment. The ultrasonic diagnostic apparatus 1 shown in FIG. 1 includes an apparatus body 10 and an ultrasonic probe 20. The apparatus body 10 is connected to an input device 30 and a display 40. The apparatus body 10 is connected to an external device 50 via a network NW.

The ultrasonic probe 20 executes an ultrasonic scan for a scan area in a living body P, which is the subject, under the control of, for example, the apparatus body 10. The ultrasonic probe 20 includes, for example, a plurality of, piezoelectric transducers, a matching layer provided in each of the piezoelectric transducers, and a backing member for preventing backward propagation of an ultrasonic wave from the piezoelectric transducers. The ultrasonic probe 20 is detachably connected to the apparatus body 10. The ultrasonic probe 20 may be provided with a button which is pressed when offset processing is performed or when an ultrasonic image freezes.

The ultrasonic probe 20 is, for example, a one-dimensional array linear probe in which a plurality of ultrasonic transducers are arranged in a predetermined direction, a two-dimensional array probe in which a plurality of piezoelectric transducers are arranged in a two-dimensional matrix, or a mechanical four-dimensional probe capable of executing an ultrasonic scan while mechanically flapping a piezoelectric transducer line in directions orthogonal to the alignment direction.

The piezoelectric transducers generate an ultrasonic wave based on a drive signal supplied from ultrasonic transmission circuitry 11 (to be described later), which is included in the apparatus body 10. An ultrasonic wave is thereby transmitted from the ultrasonic probe 20 to the living body P. When an ultrasonic wave is transmitted from the ultrasonic probe 20 to the living body P, the transmitted ultrasonic wave is sequentially reflected on the acoustic impedance discontinuous surfaces in body tissue of the living body P, and is received at the piezoelectric transducers as a reflected wave signal. The amplitude of the received reflected wave signal depends on the difference in acoustic impedance between the discontinuous surfaces by which an ultrasonic wave is reflected. When a transmitted ultrasonic pulse is reflected by a moving bloodstream or a moving surface of a cardiac wall or the like, the frequency of the reflected wave signal is shifted, due to the Doppler effect, depending on the velocity component of the moving object in the ultrasonic transmission direction. The ultrasonic probe 20 receives a reflected wave signal from the living body P, and converts it into an electrical signal.

FIG. 1 only shows a connection relationship between the apparatus body 10 and an ultrasonic probe 20 used for an ultrasonic scan. However, a plurality of ultrasonic probes may be connected to the apparatus body 10. Which of the connected ultrasonic probes is to be used for an ultrasonic scan can be selected at will via a switching operation.

The apparatus body 10 generates an ultrasonic image based on a reflected wave signal received by the ultrasonic probe 20. The apparatus body 10 includes ultrasonic transmission circuitry 11, ultrasonic reception circuitry 12, internal storage circuitry 13, an image memory 14, an input interface 15, an output interface 16, a communication interface 17, and processing circuitry 18.

The ultrasonic transmission circuitry 11 is a processor that supplies a drive signal to the ultrasonic probe 20. The ultrasonic transmission circuitry 11 is implemented by, for example, a pulse generator 111, transmission delay circuitry 112, and pulser circuitry 113. The pulse generator 111 repeatedly generates a rate pulse for forming a transmission ultrasonic wave at a predetermined pulse repetition frequency (PRF). The transmission delay circuitry 112 provides each rate pulse generated by the pulse generator 111 with a delay time for each piezoelectric transducer, which is necessary for converging the ultrasonic wave generated by the ultrasonic probe 20 into a beam form and thereby determining a transmission directivity. The transmission direction or the transmission delay time for determining the transmission direction is stored in the internal storage circuitry 13, and is referred to upon transmission. The pulser circuitry 113 applies a drive signal (drive pulse) to the ultrasonic transducers provided in the ultrasonic probe 20 at a timing based on the rate pulse. By varying the delay time provided to each rate pulse by the transmission delay circuitry 112, the transmission direction from the piezoelectric transducer surface can be freely adjusted.

The ultrasonic transmission circuitry 11 has a function of instantly changing the transmission frequency, transmission drive voltage, or the like to execute a predetermined scan sequence based on an instruction of the processing circuitry 18. In particular, the function of changing the transmission drive voltage is implemented by linear-amplifier-type originating circuitry capable of instantly changing the value or a mechanism for electrical switching between a plurality of power-supply units.

The ultrasonic reception circuitry 12 is a processor that performs various types of processing on the reflected wave signal received by the ultrasonic probe 20 and thereby generates a reception signal. The ultrasonic reception circuitry 12 is implemented by, for example, a preamplifier 121, an A/D converter 122, a demodulator 123, and a beam former 124.

The preamplifier 121 performs gain correction processing by amplifying the reflected wave signal received by the ultrasonic probe 20 for each channel. At this time, the preamplifier 121 changes the gain value in accordance with, for example, a predetermined time response. The time response of the gain applied to the reception signal at the preamplifier 121 is stored in the internal storage circuitry 13.

The A/D converter 122 converts the gain-corrected reflected wave signal into a digital signal. The demodulator 123 demodulates the digital signal, thereby converting the digital signal into an in-phase signal (I-signal; I: In-phase) and a quadrature signal (Q-signal; Q: Quadrature-phase). The beam former 124 provides the I-signal and Q-signal (hereinafter referred to as an "IQ signal") with a delay time necessary for determining a reception directivity. The beam former 124 sums IQ signals each provided with a delay time. Through the processing of the beam former 124, a reception signal with an enhanced reflected component in a direction corresponding to the reception directivity is generated.

The internal storage circuitry 13 includes, for example, a magnetic or optical storage medium, or a processor-readable storage medium such as a semiconductor memory. The internal storage circuitry 13 stores, for example, a program for realizing ultrasonic transmission/reception. The internal storage circuitry 13 also stores various types of data such as diagnostic information, a scan sequence, a diagnostic protocol, an ultrasonic transmission/reception condition, a signal processing condition, an image generation condition, an image processing condition, a body mark generation program, a display condition, and a conversion table or the like that presets, for each diagnosis site, the range of color data used for visualization. The programs and various types of data may be stored in advance in, for example, the internal storage circuitry 13, or may be stored and distributed in a non-transitory storage medium, read from the non-transitory storage medium, and installed in the internal storage circuitry 13.

The internal storage circuitry 13 stores the reception signal generated in the ultrasonic reception circuitry 12 and various ultrasonic image data items, etc. generated in the processing circuitry 18, in accordance with an operation input via the input interface 15. The internal storage circuitry 13 may transfer the stored data to the external device 50, etc. via the communication interface 17.

The internal storage circuitry 13 may be, for example, a CD-ROM drive, a DVD drive, or a drive which reads and writes various types of information from and in a portable storage medium, such as a flash memory. The internal storage circuitry 13 may write the stored data in a portable storage medium and store the data in the external device 50 via the portable storage medium.

The image memory 14 includes, for example, a magnetic storage medium, an optical storage medium, or a processor-readable storage medium such as a semiconductor memory. The image memory 14 stores image data corresponding to a plurality of frames immediately before a freeze operation input via the input interface 15. The image data stored in the image memory 14 is, for example, continuously displayed (cine-displayed).

The internal storage circuitry 13 and the image memory 14 need not necessarily be implemented by storage devices independent from each other. The internal storage circuitry 13 and the image memory 14 may be implemented by a single storage device. Each of the internal storage circuitry 13 and the image memory 14 may be implemented by a plurality of storage devices.

The input interface 15 receives various instructions from the operator via the input device 30. The input device 30 is, for example, a mouse, a keyboard, a panel switch, a slider switch, a trackball, a rotary encoder, an operation panel, or a touch command screen (TCS). The input interface 15 is connected to the processing circuitry 18 via, for example, a bus, and converts an operation instruction input by the operator into an electrical signal and outputs the electrical signal to the processing circuitry 18. The input interface 15 is not limited to the one connected to a physical operational component, such as a mouse or a keyboard. Examples of the input interface include circuitry that receives an electrical signal corresponding to an operation instruction input from an external input device provided separately from the ultrasonic diagnostic apparatus 1, and subsequently outputs the electrical signal to the control circuitry 18.

The output interface 16 is an interface for outputting, for example, an electrical signal from the processing circuitry 18 to the display 40. The display 40 can be any display such as a liquid crystal display, an organic EL display, an LED display, a plasma display, or a CRT display. The output interface 16 is connected to the processing circuitry 18 via, for example, a bus, and outputs an electrical signal from the processing circuitry 18 to the display.

The communication interface 17 is connected to the external device 50 via, for example, the network NW, and performs data communication with the external device 50.

The processing circuitry 18 is, for example, a processor that functions as a nerve center of the ultrasonic diagnostic apparatus 1. The processing circuitry 18 executes a program stored in the internal storage circuitry 13, thereby implementing a function corresponding to the program. The processing circuitry 18 has, for example, a B-mode processing function 181, a Doppler processing function 182, an elastography processing function 183, an ATI processing function 184, an image generation function 185, a display control function 186, and a system control function 187. Described in the present embodiment is the case where a single processor implements the B-mode processing function 181, the Doppler processing function 182, the elastography processing function 183, the ATI processing function 184, the image generation function 185, the display control function 186, and the system control function 187; however, the embodiment is not limited to such a case. A plurality of independent processors may constitute processing circuitry in combination, and execute respective programs to implement the B-mode processing function 181, the Doppler processing function 182, the elastography processing function 183, the ATI processing function 184, the image generation function 185, the display control function 186, and the system control function 187. Dedicated hardware circuitry capable of executing each function may be incorporated.

The B-mode processing function 181 is a function for generating B-mode data based on the reception signal received from the ultrasonic reception circuitry 12.

Specifically, through the B-mode processing function 181, the processing circuitry 18 performs envelope detection processing, logarithmic compression processing and the like on the reception signal received from the ultrasonic reception circuitry 12 to generate data (B-mode data) that expresses signal intensity by brightness. The generated B-mode data is stored in a raw data memory (not shown) as B-mode raw data on a two-dimensional ultrasonic scanning line (raster).

The Doppler processing function 182 is a function for analyzing the frequency of the reception signal received from the ultrasonic reception circuitry 12, and thereby generating data (Doppler data) obtained by the extraction of motion information based on a Doppler effect of a moving object in an imaging region of interest (ROI) set in the scan area. The generated Doppler data is stored in a raw data memory (not shown) as Doppler raw data on a two-dimensional ultrasonic scanning line.

The elastography processing function 183 is a function for calculating an index value indicating elasticity or viscosity of tissue in the subject P based on the reception signal received from the ultrasonic reception circuitry 12. Specifically, through the elastography processing function 183, the processing circuitry 18 calculates a displacement caused in the subject P using, for example, phase information included in the reception signal received from the ultrasonic reception circuitry 12. The processing circuitry 18 calculates an index value indicating elasticity of tissue in the subject P based on the calculated displacement. The index value indicating elasticity of tissue is, for example, a propagation speed of a shear wave generated in the subject P. Hereinafter, the "propagation speed of the shear wave" will be referred to as a "shear wave speed". The shear wave speed is fast in hard tissue and slow in soft tissue if the living body has uniform density. The processing circuitry 18 may calculate a Young's modulus or a shear elastic modulus from the shear wave speed, and use the calculated Young's modulus or shear elastic modulus as the index value indicating elasticity of tissue. The arrival time of the shear wave may be used as the index value indicating elasticity of tissue.

The processing circuitry 18 calculates the index value indicating viscosity of tissue in the subject P based on, for example, the relationship between the shear wave frequency and the shear wave speed. The index value indicating viscosity of tissue is, for example, a slope of phase speed distribution. The processing circuitry 18 may calculate a viscosity coefficient, and use the calculated viscosity coefficient as the index value indicating viscosity of tissue.

The ATI processing function 184 is a function for calculating an index value indicating an attenuation of an ultrasonic wave in the subject P based on the reception signal received from the ultrasonic reception circuitry 12. Specifically, through the ATI processing function 184, the processing circuitry 18 performs envelope detection processing, logarithmic compression processing, and the like on the reception signal received from the ultrasonic reception circuitry 12 to generate attenuation image B-mode data that expresses signal intensity by brightness. The processing circuitry 18 performs a correction corresponding to a gain set in the preamplifier 121 on the attenuation image B-mode data, and calculates an index value indicating an attenuation using the corrected attenuation image B-mode data. The index value indicating an attenuation is, for example, an attenuation coefficient.

The image generation function 185 is a function for generating various types of ultrasonic image data based on data generated through the B-mode processing function 181, the Doppler processing function 182, the elastography processing function 183, and/or the ATI processing function 184. Specifically, through the image generation function 185, the processing circuitry 18 executes, for example, a raw-pixel conversion, such as a coordinate conversion corresponding to the mode of the ultrasonic scan by the ultrasonic probe 20, on B-mode raw data stored in the raw data memory to generate B-mode image data consisting of pixels.

The processing circuitry 18 also executes, for example, a raw-pixel conversion on Doppler raw data stored in the raw data memory to generate Doppler image data that visualizes bloodstream information. The Doppler image data is speed image data, dispersion image data, power image data, or image data from a combination of aforementioned data.

The processing circuitry 18 also generates elasticity image data that expresses the hardness of living tissue in color based on, for example, the index value indicating elasticity calculated by the elastography processing function 183. The processing circuitry 18 generates viscosity image data that expresses the viscosity of living tissue in color based on, for example, the index value indicating viscosity calculated by the elastography processing function 183. The processing circuitry 18 generates propagation image data that expresses the shear wave propagation in color based on, for example, the shear wave speed calculated by the elastography processing function 183.

The processing circuitry 18 also executes, for example, a raw-pixel conversion on the attenuation image B-mode raw data calculated by the ATI processing function 184 to generate attenuation image B-mode image data. The processing circuitry 18 generates attenuation image data that expresses an attenuation of the shear wave in color based on, for example, the index value indicating an attenuation calculated by the ATI processing function 184.

The display control function 186 is a function for causing the display 40 to display images based on various types of ultrasonic image data generated by the image generation function 185, and is an example of the display controller. Specifically, through the display control function 186, the processing circuitry 18 controls a display on the display 40 of an image based on B-mode image data, attenuation image B-mode image data, elasticity image data, viscosity image data, propagation image data, attenuation image data generated through the image generation function 185, or image data including at least two types of the aforementioned image data. More specifically, the processing circuitry 18 simultaneously display, by a four-screen simultaneous display, for example, a B-mode image, an attenuation image B-mode image, an elasticity image (SWE color), a viscosity image (SWD color), a propagation image (SWE Propagation), and an attenuation image (ATI color) based on B-mode image data, attenuation image B-mode image data, elasticity image data, viscosity image data, propagation image data, and attenuation image data.

Through the display control function 186, the processing circuitry 18, for example, converts (scan-converts) a scanning line signal sequence of an ultrasonic scan into a scanning line signal sequence of a video format representatively used by television, etc. to generate display image data. The processing circuitry 18 may also perform various types of processing, such as dynamic range, brightness, contrast, γ curve corrections, and an RGB conversion, on the display image data. The processing circuitry 18 may also add supplementary information, such as textual information of various parameters, a scale, or a body mark, to the display image data. The processing circuitry 18 may also generate a user interface (graphical user interface (GUI)) to allow the operator to input various instructions through the input device, and cause the display 40 to display the GUI.

The system control function 187 is a function for controlling basic operations of the ultrasonic diagnostic apparatus 1, such as input/output and ultrasonic transmission/reception. Through the system control function 187, the processing circuitry 18 receives via, for example, the input interface 15, an instruction to select various imaging modes. Various imaging modes include, for example, a B-mode, a Doppler mode, an elastography (shear wave elastography (SWE)) mode, an attenuation imaging (ATI) mode, and an SWE+ATI mode.

The elastography mode according to the present embodiment is an imaging mode in which acoustic radiation force is applied to living tissue by the ultrasonic probe on a body surface to cause a displacement by a shear wave, and the displacement is observed over time at each point in a scanning cross section. The attenuation imaging mode is an imaging mode in which, when it can be assumed that scatterer distribution in tissue is uniform, the attenuation of an ultrasonic wave at each position in the depth direction is observed by examining the change of the reflected wave signal in the depth direction. The SWE+ATI mode is, for example, an imaging mode in which the elastography mode and the attenuation imaging mode are successively performed.

FIGS. 2 to 5 are a schematic view showing an example of the scan sequence of the SWE+ATI mode according to the present embodiment. In the SWE+ATI mode, the elastography mode and the attenuation imaging mode need not necessarily be successively performed. For example, the SWE+ATI mode need only include the elastography mode and the attenuation imaging mode in the same scan sequence.

In the scan sequence example shown in FIG. 2, a scan for acquiring B-mode data (B-mode scan) and a scan for acquiring a reception signal for performing elastography processing (SWE scan) are performed. Then, after a cooling time, a scan for acquiring a reception signal for performing attenuation imaging processing (ATI scan) is performed.

The cooling time is a period of time for lowering the heat generated at the probe, and is provided after a scan in which the probe generates a large amount of heat (such as the SWE scan). During the cooling time, a scan is not executed in principle; however, as long as the sudden rise in temperature due to the scan performed immediately before (such as the SWE scan) can be reversed, another scan may be executed.

Another scan includes, for example, a low-intensity B-mode scan. Usually, some heat generation is expected even by the low-intensity B-mode scan. However, the energy of radiation due to the difference between the probe temperature, which has rapidly risen, and the external temperature is larger than the energy of the aforementioned heat generation; as a result, the probe temperature can be lowered. The probe temperature can be lowered similarly when a B-mode scan with a lower frame rate is performed instead of the low-intensity B-mode scan.

For example, if no scan is executed during the cooling time, the cooling time can be shortened, but the ultrasonic image displayed on the display 40 is not updated. On the other hand, if a low-intensity B-mode scan is executed during the cooling time, the cooling time lengthens, but the ultrasonic image displayed on the display 40 is updated. The update of the ultrasonic image during the cooling time enables the user to ascertain the position at which the probe is in contact, and can be used for the subsequent positioning.

The order of scans in the scan sequence is not limited to the order shown in FIG. 2, and may be the orders shown in FIGS. 3 to 5. In the scan sequence example shown in FIG. 3, a cooling time is provided after the B-mode scan, SWE scan, and ATI scan. In the scan sequence example shown in FIG. 4, a cooling time is provided after the B-mode scan, ATI scan, and SWE scan. In the scan sequence shown in FIG. 5, a cooling time is provided after the ATI scan, B-mode scan, and SWE scan.

To sum up the above-described scan sequences, the scan sequence of FIG. 2 includes a cooling time immediately after the SWE scan, and includes the ATI scan immediately after the cooling time. The scan sequence of FIG. 3 includes the ATI scan immediately after the SWE scan, and includes a cooling time immediately after the ATI scan. The scan sequence of FIG. 3 and that of FIG. 4 include the SWE scan and ATI scan successively provided.

The processing circuitry 18 controls each component in the ultrasonic diagnostic apparatus 1 to perform an ultrasonic scan in a selected imaging mode. Upon a change in the position of an imaging ROI set in the scan area via, for example, the input interface 15, the processing circuitry 18 performs a scan for the performance of elastography processing and a scan for the performance of attenuation imaging processing based on the changed imaging ROI.

Next, an operation of the ultrasonic diagnostic apparatus 1 configured as described above to cause the display 40 to display images based on various types of ultrasonic image data will be described.

FIG. 6 is a flowchart showing an example of an operation performed when the ultrasonic diagnostic apparatus 1 shown in FIG. 1 causes the display 40 to display a plurality of images based on various types of ultrasonic image data. In the description of FIG. 6, the operation of the ultrasonic diagnostic apparatus 1 of the case where the SWE+ATI mode is selected and where a plurality of images are simultaneously displayed by a four-screen simultaneous display will be taken as an example.

First, the operator selects, for example, the SWE+ATI mode, and inputs a start instruction to start the selected SWE+ATI mode via the input interface 15.

(Step S61)

When the start instruction to start the SWE+ATI mode is input, the processing circuitry 18 of the ultrasonic diagnostic apparatus 1 executes the system control function 187. Through the system control function 187, the processing circuitry 18 performs scans for the SWE+ATI mode in step S61.

Specifically, the processing circuitry 18 reads a scan sequence for the selected SWE+ATI mode from the internal storage circuitry 13. In the description of FIG. 6, let us assume that the scan order is set for the SWE+ATI mode as shown in FIG. 2. The processing circuitry 18 reads, from the internal storage circuitry 13, an ultrasonic transmission/reception condition for the B-mode scan set in the first place in the scan sequence of the SWE+ATI mode. The processing circuitry 18 sets the read ultrasonic transmission/reception condition in the ultrasonic transmission circuitry 11. An ultrasonic wave is thereby transmitted from the ultrasonic probe 20 to the subject P based on the ultrasonic transmission/reception condition for B-mode scan.

The ultrasonic wave transmitted from the ultrasonic probe 20 to the subject P is sequentially reflected by acoustic impedance discontinuous surfaces in body tissue of the subject P, and is received at the ultrasonic probe 20 as a reflected wave signal. The ultrasonic reception circuitry 12 executes various types of processing on the reflected wave signal received by the ultrasonic probe 20 to generate a first reception signal. The generated first reception signal is retained in, for example, a buffer (not shown).

Upon completion of the B-mode scan, the processing circuitry 18 reads, from the internal storage circuitry 13, an ultrasonic transmission/reception condition for the elastography scan set in the second place in the scan sequence of the SWE+ATI mode. The processing circuitry 18 sets the read ultrasonic transmission/reception condition in the ultrasonic transmission circuitry 11. The ultrasonic transmission/reception condition for the elastography mode scan is set so that, for example, a push pulse is transmitted to an imaging ROI, and then a tracking pulse is transmitted thereto. A reference pulse is a pulse for acquiring a reference of displacement. The push pulse is a pulse for generating a shear wave in the subject P by acoustic radiation force, which has a longer wave train length than, for example, a normal ultrasonic wave. The tracking pulse is a pulse for observing a displacement.

The reference pulse transmitted from the ultrasonic probe 20 to the subject P is sequentially reflected by acoustic impedance discontinuous surfaces in body tissue of the subject P, and is received at the ultrasonic probe 20 as a reflected wave signal. The ultrasonic reception circuitry 12 executes various types of processing on the reflected wave signal received by the ultrasonic probe 20 to generate a second reception signal. Acoustic radiation force of the push pulse transmitted from the ultrasonic probe 20 to the subject P causes a shear wave in the living body, and propagation of the shear wave causes a displacement at a position away from the transmission position of the push pulse. The tracking pulse transmitted from the ultrasonic probe 20 to the subject P is sequentially reflected by acoustic impedance discontinuous surfaces in body tissue of the subject P, and is received at the ultrasonic probe 20 as a reflected wave signal. The ultrasonic reception circuitry 12 executes various types of processing on the reflected wave signal received by the ultrasonic probe 20 to generate a third reception signal. The generated second and third reception signals are retained in, for example, a buffer.

The force that provides a displacement to living tissue is not limited to the acoustic radiation force generated by the push pulse. For example, a displacement to living tissue may be caused by application of mechanical vibration by an external device.

Upon completion of the elastography mode scan, the processing circuitry 18 halts the processing for a predetermined cooling time. After the passage of the predetermined cooling time, the processing circuitry 18 reads, from the internal storage circuitry 13, an ultrasonic transmission/reception condition for attenuation imaging mode scan set in the third place in the scan sequence of the SWE+ATI mode. The processing circuitry 18 sets the read ultrasonic transmission condition in the ultrasonic transmission circuitry 11. As the ultrasonic transmission condition for attenuation imaging mode scan, the transmission bandwidth is determined based on the frequency characteristics of the ultrasonic probe 20. For example, the transmission bandwidth is a narrow bandwidth including a center frequency (single frequency). The transmission bandwidth is determined in accordance with the test target site.

The ultrasonic wave transmitted from the ultrasonic probe 20 to the subject P is scattered by a structure in the subject P, and is received at the ultrasonic probe 20. The preamplifier 121 of the ultrasonic reception circuitry 12 executes gain adjustment processing on the reflected wave signal received by the ultrasonic probe 20. For example, the preamplifier

121 adjusts the reflected wave signal with a gain value that changes in accordance with a predetermined time response. Specifically, the gain value is set to increase as the depth of the generation position of the reflected wave increases, for example. The time response of the gain when the reflected wave signal is adjusted by the preamplifier 121 is stored in the internal storage circuitry 13. The ultrasonic reception circuitry 12 executes various types of processing on the reflected wave signal after gain adjustment at the preamplifier 121 to generate a fourth reception signal. The generated fourth reception signal is retained in, for example, a buffer.

(Step S62)

After the scans for the SWE+ATI mode are performed, the processing circuitry 18, for example, generates B-mode data and attenuation image B-mode data based on the first to fourth reception signals generated in the respective scans, and calculates an index value indicating elasticity, an index value indicating viscosity, and an index value indicating an attenuation.

Specifically, the processing circuitry 18 first executes, for example, the B-mode processing function 181 and the elastography processing function 183 in parallel. Through the B-mode processing function 181, the processing circuitry 18 executes envelop detection processing, logarithmic compression processing, and the like on the first reception signal retained in the buffer to generate B-mode data. The generated B-mode data is stored in the raw data memory as B-mode raw data on a two-dimensional ultrasonic scanning line (raster).

Through the elastography processing function 183, the processing circuitry 18 uses, for example, the second reception signal concerning the reference pulse, which is retained in the buffer, and calculates a displacement which serves as a reference for each segmented region. For example, the processing circuitry 18 calculates the moving speeds of tissue over multiple time phases using phase information of the second reception signal. The processing circuitry 18 calculates the displacement of tissue by time-integrating the moving speeds of the multiple time phases.

Upon calculation of the displacement that serves as a reference, the processing circuitry 18 uses, for example, the third reception signal concerning the tracking pulse to calculate a displacement for each segmented region. For example, the processing circuitry 18 calculates the moving speeds of tissue over multiple time phases using phase information of the third reception signal. The processing circuitry 18 calculates the displacement of tissue by time-integrating the moving speeds of the multiple time phases.

Subsequently, the processing circuitry 18 subtracts the displacement calculated for the reference pulse from the displacement calculated for the tracking pulse to acquire a time of the maximum displacement after subtraction. The processing circuitry 18 uses the time at which the maximum displacement is acquired as an arrival time at which the shear wave arrived at the scan position. The processing circuitry 18 calculates a shear wave speed based on the arrival time of the shear wave. In addition, the processing circuitry 18 calculates a Young's modulus based on the shear wave speed. The processing circuitry 18 uses the calculated shear wave speed and Young's modulus as an index value indicating elasticity of tissue.

Next, the processing circuitry 18 calculates a phase of each of a plurality of frequency components included in the shear wave detected based on the calculated displacements. For example, the processing circuitry 18 performs a Fourier transform on a time displacement curve representing a temporal change of displacement to calculate a phase of each frequency for each sample point. The processing circuitry 18 uses the phase calculated for each sample point to calculate a phase speed for each frequency component. The processing circuitry 18 calculates, for example, a slope of phase speed distribution, which represents the amount of change of the calculated phase speed in the frequency direction. The processing circuitry 18 uses the calculated slope of the phase speed distribution as an index value indicating viscosity of tissue.

Upon generation of B-mode data through the B-mode processing function 181, the processing circuitry 18 executes the ATI processing function 184. Through the ATI processing function 184, the processing circuitry 18 executes envelop detection processing, logarithmic compression processing, and the like on the fourth reception signal retained in the buffer to generate attenuation image B-mode data. At this time, to acquire a correct ultrasonic attenuation in the subject P, the processing circuitry 18 limits the reception bandwidth to a narrow band around the transmission center frequency and sets the limited reception bandwidth so as not to change in the depth direction. This enables the removal of a tissue harmonic signal component. The generated attenuation image B-mode data is stored in the raw data memory as attenuation image B-mode raw data on a two-dimensional ultrasonic scanning line.

Next, the processing circuitry 18 executes, for example, gain correction processing to cancel the gain adjustment on the attenuation image B-mode raw data based on the time response of the gain stored in the internal storage circuitry 13. Namely, the processing circuitry 18 makes a correction that cancels both of the reference gain and the adjustment amount corresponding to the position of occurrence of echo on the attenuation image B-mode raw data. The processing circuitry 18 uses the attenuation image B-mode raw data after the gain correction to calculate an index value indicating an attenuation. Specifically, when it can be assumed that, for example, the scatterer distribution in tissue is uniform, the processing circuitry 18 calculates a slope of the depth direction within a predetermined depth range in the corrected attenuation image B-mode raw data. The processing circuitry 18 multiplies the calculated slope in the depth direction by a transmission/reception frequency to calculate an attenuation coefficient. The processing circuitry 18 uses the calculated attenuation coefficient as an index value indicating an attenuation.

(Step S63)

After generation of B-mode data and attenuation image B-mode data and calculation of the index value indicating elasticity, the index value indicating viscosity, and the index value indicating an attenuation, the processing circuitry 18 generates various types of ultrasonic image data based on the generated data and the calculated index values.

Specifically, after generating B-mode data and attenuation image B-mode data and calculating a shear wave speed, a lope of phase speed distribution, and an attenuation coefficient, the processing circuitry 18 executes the image generation function 185. Through the image generation function 185, the processing circuitry 18 executes, for example, a raw-pixel conversion on the B-mode raw data stored in the raw data memory to generate B-mode image data. The processing circuitry 18 also executes, for example, a raw-pixel conversion on the attenuation image B-mode raw data stored in the raw data memory to generate attenuation image B-mode image data.

The processing circuitry 18 also generates elasticity image data that visualizes the shear wave speed in the imaging ROI based on the calculated shear wave speed and a preset color map. The processing circuitry 18 generates elasticity image data that visualizes the Young's modulus in the imaging ROI based on the calculated Young's modulus and a preset color map. The processing circuitry 18 also generates viscosity image data that visualizes the slope of phase speed distribution in the imaging ROI based on the calculated slope of phase speed distribution and a preset color map. The processing circuitry 18 also generates line image data in which the points of approximately the same shear wave arrival time are connected by a line. The processing circuitry 18 generates propagation image data that visualizes propagation of the shear wave in the imaging ROI based on line image data and a preset color map. The processing circuitry 18 generates attenuation image data that visualizes the attenuation coefficient in the imaging ROI based on the calculated attenuation coefficient and a preset color map.

(Step S64)

Upon generation of various types of ultrasonic image data, the processing circuitry 18 causes the display 40 to display an image based on each type of data.

Specifically, upon generation of, for example, the B-mode image data, attenuation image B-mode image data, elasticity image data, viscosity image data, propagation image data, and attenuation image data, the processing circuitry 18 executes the display control function 186. Through the display control function 186, the processing-circuitry 18 simultaneously display, by a four-screen simultaneous display, a B-mode image, an attenuation image B-mode image, an elasticity image, a viscosity image, a propagation image, and an attenuation image based on the B-mode image data, attenuation image B-mode image data, elasticity image data, viscosity image data, propagation image data, and attenuation image data, respectively.

Figure 7:
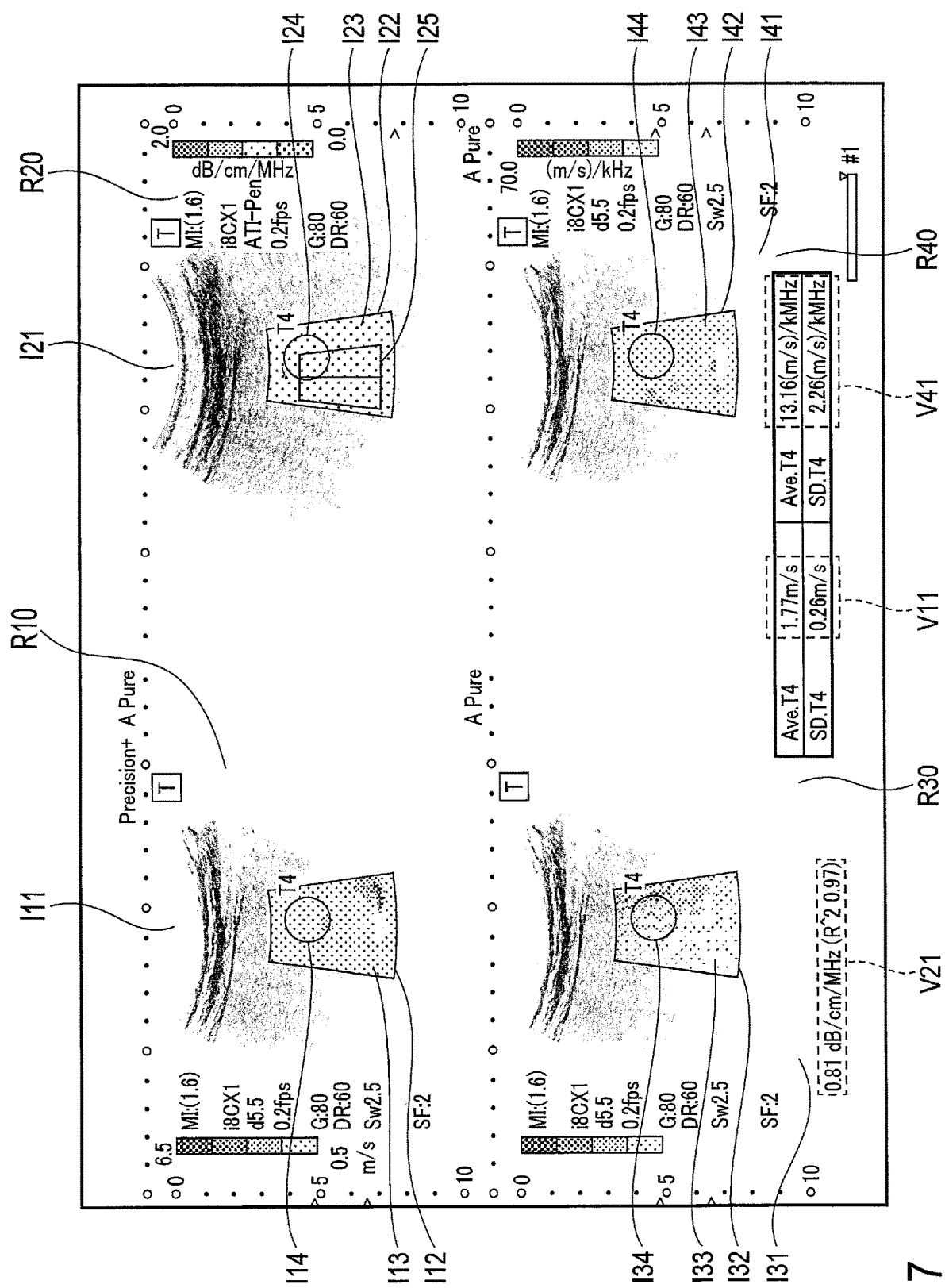
FIG. 7 is a diagram showing a four-screen simultaneous display which is displayed on the display shown in FIG. 1.

FIG. 7 is a schematic diagram showing an example of the four-screen simultaneous display on the display 40 shown in FIG. 1. In the layout shown in FIG. 7, four types of images are displayed in four display regions R10 to R40, respectively.

In display region R10, an imaging ROI I12 is set in a B-mode image I11, and elasticity image I13 overlaps the imaging ROI I12. A first measurement ROI I14 overlaps the elasticity image I13. The numerical value group V11 shown in FIG. 7 includes an average value and standard deviation (SD value) of shear wave speeds in the first measurement ROI I14. The index value shown in the display region R10 is not limited to the shear wave speed, and may be switched to the Young's modulus. At this time, the numerical value group V11 includes an average value and standard deviation (SD value) of Young's moduli in the first measurement ROI I14.

In display region R20, an imaging ROI I22 is set in an attenuation image B-mode image I21, and an attenuation image I23 overlaps the imaging ROI I22. A first measurement ROI I24 and second measurement ROI I25 overlap the attenuation image I23. The numerical value group V21 shown in FIG. 7 includes a representative value of attenuation coefficients in the second measurement ROI I25. The representative value is, for example, an average value, maximum value, minimum value, or the like of the attenuation coefficients in the second measurement ROI I25. The representative value of the attenuation coefficients may be accompanied by an R2-th root value (coefficient of determination).

In display region R30, an imaging ROI I32 is set in a B-mode image I31, and a propagation image I33 overlaps the imaging ROI I32. A first measurement ROI I34 overlaps the propagation image I33.

In display region R40, an imaging ROI I42 is set in a B-mode image I41, and a viscosity image I43 overlaps the imaging ROI I42. A first measurement ROI I44 overlaps the viscosity image I43. The numerical value group V41 shown in FIG. 7 includes an average value and standard deviation (SD value) of phase speed distribution in the first measurement ROI I44.

The first measurement ROIs I14 to I44 shown in the display regions R10 to R40 have the same shape and size. The positions of the first measurement ROIs I14 to I44 move in conjunction with one another on the B-mode images I11, I31, and I41 and attenuation image B-mode image I21. Namely, if one of the first measurement ROIs I14 to I44 is moved in a given direction by a given distance via the input interface 15, the processing circuitry 18 moves the other three first measurement ROIs in the same direction by the same distance through the display control function 186.

Figure 8:
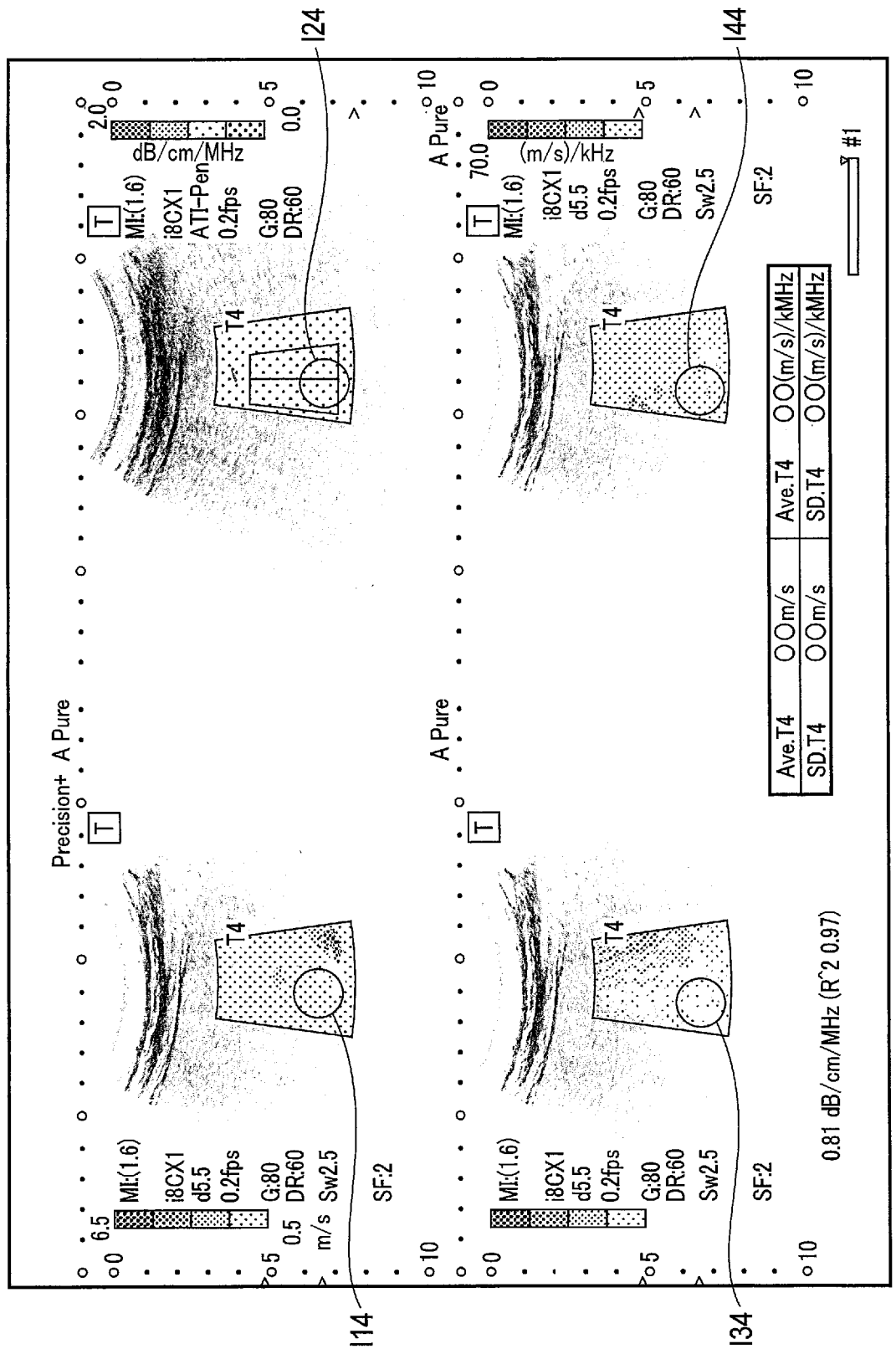
FIG. 8 is a diagram showing that the positions of first measurement ROIs are moved in conjunction with one another.

For example, the operator refers to the propagation image I33, and moves first measurement ROI I34 to another region in imaging ROI I32 in which a shear wave is clearly shown. The processing circuitry 18 then moves first measurement ROIs I14, I24, and I44 to the positions in imaging ROI I12, I22, and I42 corresponding to the position of first measurement ROI I34. FIG. 8 is a schematic view showing that the positions of the first measurement ROIs I14 to I44 are moved in conjunction with one another.

Figure 9:
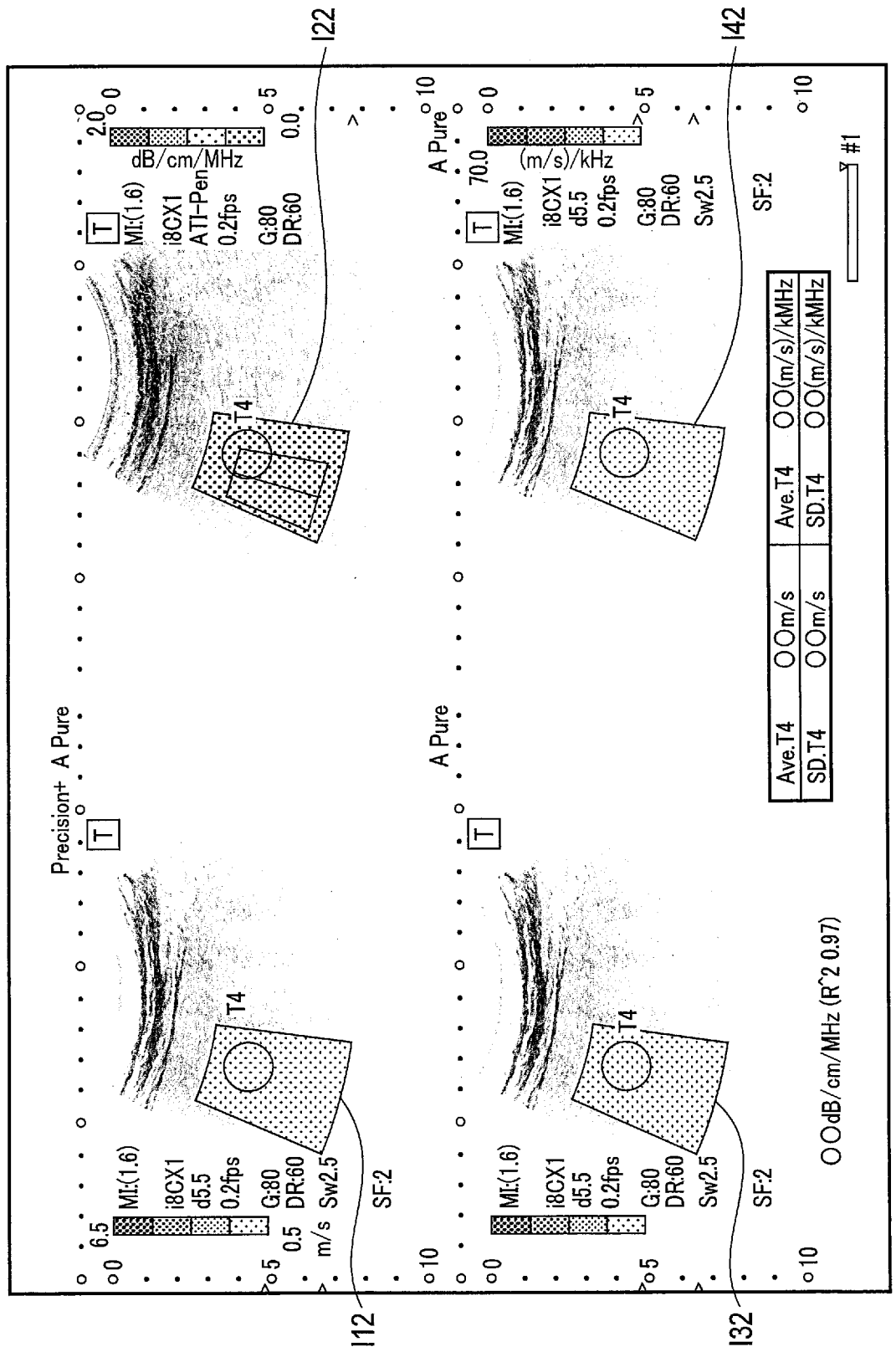
FIG. 9 is a diagram showing that the positions of imaging ROIs are moved in conjunction with one another.

The first measurement ROIs I12, I32, and I42 shown in display regions R10, R30, and R40 have the same shape and size. Imaging ROI I22 may have the same shape and size as imaging ROIs I12, I32, and I42, or may have a different shape and size therefrom. The positions of imaging ROIs I12 to I42 move in conjunction with one another on B-mode images I11, I31, and I41 and attenuation image B-mode image I21. Namely, when the position of the imaging ROI is changes in at least one of the B-mode scan, elastography mode scan, and attenuation imaging mode scan, the processing circuitry 18 changes, through the display control function 186, the positions of the imaging ROIs in the other scans in accordance with the changed position. FIG. 9 is a schematic view showing that the positions of the imaging ROIs I12 to I42 are moved in conjunction with one another.

As described above, according to the first embodiment, the processing circuitry 18 causes, through the display control function 186, the display 40 to display an elasticity image I13 or viscosity image I43 concerning the index value indicating elasticity or viscosity, and calculated based on the displacement of tissue by a shear wave that propagates in a living body, as well as an attenuation image I23 concerning the index value indicating an attenuation of a reflected wave signal of an ultrasonic wave applied into the living body. The processing circuitry 18 then moves imaging ROIs I12 and I42 for acquiring an index value indicating elasticity or viscosity and imaging ROI I22 for acquiring an index value indicating an attenuation in conjunction with one another. The processing circuitry 18 also moves regions of interest (measurement ROIs I14 and I44) which overlap the elasticity image I13 or viscosity image I43 and a region of interest (measurement ROI I24) which overlaps the attenuation image I23, in conjunction with one another. Accordingly, the elasticity image I13, viscosity image I43, and attenuation image I23 can be displayed on the display 40 as associated images of approximately the same time phase and approximately the same cross section.

In the first embodiment, the elasticity image I13 or viscosity image I43 and the attenuation image I23 are acquired in the SWE+ATI mode, i.e., in the same scan sequence. In general, the elastography sequence is executed separately from the attenuation imaging sequence. Therefore, execution of the sequences may take time, and cross sections of collected images may be slightly displaced from each other. In the present embodiment, the elasticity image I13 or viscosity image I43 and the attenuation image I23 are acquired in the same scan sequence; therefore, the burden placed on the operator is small, and the displacement between scan cross sections can be suppressed.

In addition, in the first embodiment, the processing circuitry 18 successively performs the elastography mode scan and the attenuation imaging mode scan in the scan sequence. Accordingly, the time lag between the elastography mode scan and the attenuation imaging mode scan can be reduced, and the displacement between scan cross sections can be further suppressed.

Described in the above embodiment is the case where the propagation image I33 is displayed together with the elasticity image I13, the attenuation image I23, and the viscosity image I43. The propagation image I33 is effective in determining the positions of the first measurement ROIs I14 to I44, but need not necessarily be displayed.

Other Embodiments

Described in the first embodiment is the case where a B-mode image, an attenuation image B-mode image, an elasticity image, a viscosity image, and an attenuation image are displayed on the display 40 which is connected to the ultrasonic diagnostic apparatus 1. However, the embodiment is not limited to this. The B-mode image, attenuation image B-mode image, elasticity image, viscosity image, and attenuation image may be displayed on a display 22 of an analysis apparatus 2 connected to the ultrasonic diagnostic apparatus 1 and an image storage apparatus (picture archiving and communication system (PACS)) 3 for managing various types of medical image data.

Figure 10:
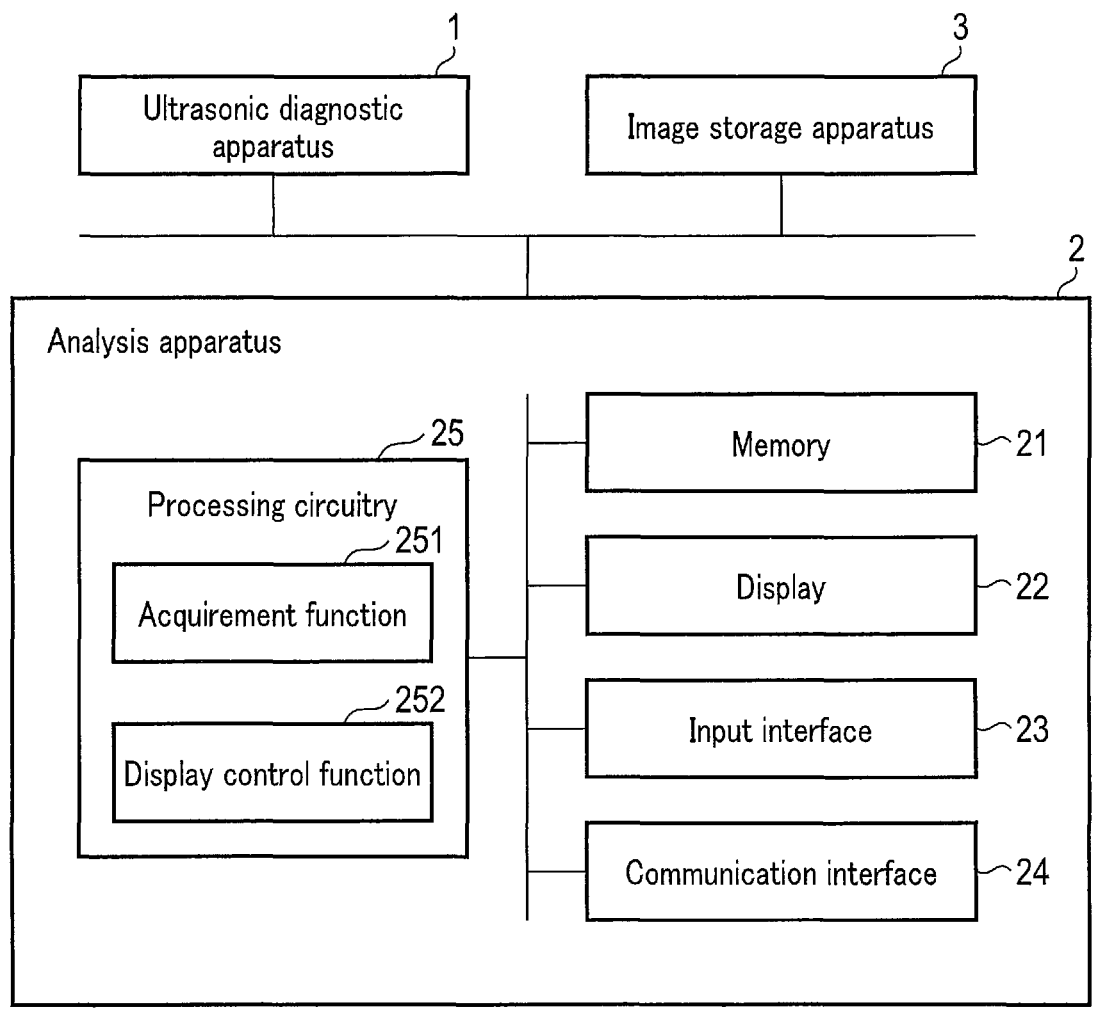
FIG. 10 is a block diagram showing a functional configuration of an analysis apparatus according to another embodiment.

FIG. 10 is a block diagram showing an example of a functional configuration of an analysis apparatus 2 according to another embodiment. The analysis apparatus 2 shown in FIG. 10 includes a memory 21, a display 22, an input interface 23, a communication interface 24, and processing circuitry 25.

The processing circuitry 25 is, for example, a processor that functions as a nerve center of the analysis apparatus 2. The processing circuitry 25 executes a program stored in the memory 21, thereby implementing a function corresponding to the program. The processing circuitry 25 has, for example, an acquisition function 251 and a display control function 252. Described in the present embodiment is the case where a single processor implements the acquisition function 251 and the display control function 252; however, the embodiment is not limited to such a case. For example, processing circuitry may be configured by combining a plurality of independent processors that execute respective programs to implement the acquisition function 251 and display control function 252. Dedicated hardware circuitry capable of executing each function may be incorporated.

The acquisition function 251 is a function for acquiring image data from the ultrasonic diagnostic apparatus 1 or the image storage apparatus 3. Specifically, through the acquisition function 251, the processing circuitry 25 acquires B-mode image data, attenuation image B-mode image data, elasticity image data, viscosity image data, and attenuation image data generated in the SWE+ATI mode in the ultrasonic diagnostic apparatus 1, in accordance with an instruction input via the input interface 23. In accordance with an instruction input via the input interface 23, the processing circuitry 25 also acquires B-mode image data, attenuation image B-mode image data, elasticity image data, viscosity image data, and attenuation image data generated in the SWE+ATI mode and stored in the image storage apparatus 3. The image storage apparatus 3 stores, for example, B-mode image data, attenuation image B-mode image data, elasticity image data, viscosity image data, and attenuation image data with an identifier that enables identification of the fact that the data is generated in the same SWE+ATI mode assigned thereto.

The processing circuitry 25 may acquire propagation image data generated in the same SWE+ATI mode from the ultrasonic diagnostic apparatus 1 or the image storage apparatus 3.

The display control function 252 is a function for causing the display 22 to display images based on various types of ultrasonic image data acquired through the acquisition function 251. Specifically, through the display control function 252, the processing circuitry 25 controls a display on the display 22 of an image based on B-mode image data, attenuation image B-mode image data, elasticity image data, viscosity image data, or attenuation image data acquired through the acquisition function 251, or image data including at least two types of the aforementioned image data. More specifically, the processing circuitry 25 simultaneously display a B-mode image, an attenuation image B-mode image, an elasticity image, a viscosity image, and an attenuation image based on the B-mode image data, attenuation image B-mode image data, elasticity image data, viscosity image data, and attenuation image data, respectively. The processing circuitry 25 may cause the display 22 to simultaneously display propagation image data, acquired from the ultrasonic diagnostic apparatus 1 or the image storage apparatus 3, together with the above images by a four-screen simultaneous display.

The processing circuitry 25 may have, for example, a B-mode processing function, a Doppler processing function, an elastography processing function, an ATI processing function, and an image generation function. At this time, reception signals generated in the ultrasonic reception circuitry 12 are transmitted, for example, from the ultrasonic diagnostic apparatus 1 to the analysis apparatus 2.

The index value for determining tissue properties is not limited to those described above. As the index value for determining tissue properties, for example, a "speed" of a bloodstream acquired by colored Doppler technique, a "displacement" of tissue acquired by tissue Doppler imaging (TDI), a "luminance local variance", which is a degree of deviation from the Rayleigh distribution of the signal amplitude distribution of reception signals, or the like can be applied.

In addition to the index value acquired by the ultrasonic diagnostic apparatus 1, for example, a parameter for hardness acquired by elastography using an MRI apparatus, a parameter relating to material discrimination analyzed by dual energy CT using differences in X-ray attenuation coefficient between materials, or the like can be applied. In other words, any parameters indicating tissue properties, i.e., parameters other than those used for a tomographic image of tissue in the subject, can be applied.

Other Specific Examples

In the above embodiments, the SWE+ATI mode is described as a specific example of the scan sequence;

however, the scan sequence is not limited to this. For example, a mode indicating a normalized local valiance (NLV) (NLV scan) may be added to the same scan sequence including the elastography mode and the attenuation imaging mode.

The NLV mode is a mode that enables a display of a degree of variance of the intensities of signals reflected from inside the tissue of the subject. The NLV indicates, for example, a degree of agreement between Rayleigh distribution and probability density distribution of brightness values of echo signals reflected by a liver. Hereinafter, a scan for acquiring an NLV will be referred to as an "NLV scan".

In the scan sequence including the NLV scan, a cooling time is provided, for example, after the B-mode scan, SWE scan, ATI scan, and NLV scan. The NLV scan is not limited to the above example, and the cooling time may be included at any position in each of the scan sequences of FIGS. 2 to 5. In addition, the NLV scan is a scan that turns off the filter in the B-mode scan (for example, a scan that does not perform smoothing in the time direction), and thus may be included in the B-mode scan in the scan sequence shown in FIG. 2, for example.

In the above-described embodiments, the period of the cooling time provided in the scan sequence is predetermined, but need not necessarily be so. For example, the processing circuitry 18 may set the cooling time based on at least the scan condition set in the SWE mode. Specifically, the processing circuitry 18 may calculate the quantity of heat generated in the SWE mode and set the cooling time based on the calculated quantity of heat.

According to at least one of the above-described embodiments, the ultrasonic diagnostic apparatus 1 and the analysis apparatus 2 can reduce the burden incurred when determining the tissue properties of a subject.

The term "processor" used in the above description of the embodiment means, for example, a central processing unit (CPU), a graphics processing unit (GPU), or circuitry such as an application specific integrated circuit (ASIC), or a programmable logic device (e.g., a simple programmable logic device (SPLD), a complex programmable logic device (CPLD), or a field programmable gate array (FPGA)). The processor implements a function by reading and executing a program stored in memory circuitry. Instead of storing a program in memory circuitry, a program may be directly integrated into the circuitry of a processor. In this case, the processor implements functions by reading and executing programs integrated in the circuitry. Each processor of the above embodiments is not necessarily configured as a single circuit, but may be configured by a combination of a plurality of independent circuits to implement its functions. Furthermore, a plurality of components in the above embodiment may be integrated into a single processor to implement their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus, comprising:
an ultrasonic probe; and
processing circuitry configured to
cause the ultrasonic probe to perform a first B-mode scan, an elastography scan, and an attenuation scan in a same scan sequence, wherein the elastography scan is for calculating a first index value based on a displacement of tissue by a shear wave that propagates through a living body, and the attenuation scan is for calculating a second index value that indicates an attenuation of a reflected wave signal of an ultrasonic wave applied into the living body;
generate a B-mode image based on the first B-mode scan, an elastography image based on the elastography scan, an attenuation imaging B-mode image based on the attenuation scan, and an attenuation image based on the attenuation imaging B-mode image;
cause a display device to simultaneously display, on a same screen, the B-mode image, the elastography image, the attenuation imaging B-mode image, and the attenuation image, with the B-mode image and the attenuation imaging B-mode image being displayed next to each other;
set a first imaging ROI for the elastography scan in the B-mode image;
overlay the elastography image upon the first imaging ROI;
set a second imaging ROI for the attenuation scan in the attenuation imaging B-mode image,
overlay the attenuation image upon the second imaging ROI;
automatically move the displayed second imaging ROI in conjunction with the displayed first imaging ROI or move the displayed first imaging ROI in conjunction with the displayed second imaging ROI;
overlay and display a first measurement region upon the elastography image;
overlay and display a second measurement region upon the attenuation image, the first and second measurement regions having a same size and shape;
overlay and display a third measurement region upon the attenuation image, the third measurement region having a different geometry than the first and second measurement regions; and
automatically move the displayed first measurement region and the displayed second measurement region in conjunction with each other and independently of the third measurement region.

2. The ultrasonic diagnostic apparatus according to claim 1, wherein the processing circuitry is further configured to move the first imaging ROI and the second imaging ROI in conjunction with each other.

3. The ultrasonic diagnostic apparatus according to claim 1, wherein, in the scan sequence, the first B-mode scan, the elastography scan, and the attenuation scan are successively set.

4. The ultrasonic diagnostic apparatus according to claim 1, wherein, in the scan sequence, a cooling time is set immediately after the elastography scan, and the attenuation scan is set immediately after the cooling time.

5. The ultrasonic diagnostic apparatus according to claim 1, wherein, in the scan sequence, the attenuation scan is set immediately after the elastography scan, and a cooling time is set immediately after the attenuation scan.

6. The ultrasonic diagnostic apparatus according to claim 1, wherein, in the scan sequence, a cooling time is set immediately after the elastography scan or the attenuation scan, and a third scan, which differs from the elastography scan and attenuation scan, is performed during the cooling time.

7. The ultrasonic diagnostic apparatus according to claim 1, wherein the scan sequence further includes a cooling time.

8. The ultrasonic diagnostic apparatus of claim 1, wherein the processing circuitry is further configured to calculate a statistical value of the first index value in the first measurement region and a representative value of the second index value in the third measurement region, and cause the display device to display values representing the statistical value of the first index value and the representative value of the second index value.

9. The ultrasonic diagnostic apparatus according to claim 2, wherein the processing circuitry is further configured to:
generate a propagation image indicating propagation of the shear wave; and
move a third imaging ROI for acquiring the propagation image and the first and second imaging ROIs in conjunction with one another, or move the third imaging ROI that overlaps the propagation image and the first and second imaging ROIs in conjunction with one another.

10. The ultrasonic diagnostic apparatus according to claim 6, wherein the third scan is a second B-mode scan generating a lower amount of heat in comparison with the elastography scan and the attenuation scan.

11. The ultrasonic diagnostic apparatus according to claim 6, wherein the third scan is a second B-mode scan having a lower intensity than the first B-mode scan.

12. The ultrasonic diagnostic apparatus according to claim 6, wherein the third scan is a second B-mode scan having a lower frame rate than the first B-mode scan.

* * * * *